United States Patent
Adamy et al.

(10) Patent No.: US 12,023,401 B2
(45) Date of Patent: *Jul. 2, 2024

(54) SULFATE-FREE PERSONAL CARE COMPOSITIONS AND METHODS FOR USING SUCH COMPOSITIONS

(71) Applicant: RHODIA OPERATIONS, Paris (FR)

(72) Inventors: Monique Martine Françoise Adamy, Asnières-sur-seine (FR); Jennifer Jessika Cazette, Sucy-en-brie (FR)

( * ) Notice: Subject to any disclaimer, the term of this patent is extended or adjusted under 35 U.S.C. 154(b) by 47 days.

This patent is subject to a terminal disclaimer.

(21) Appl. No.: 17/480,355

(22) Filed: Sep. 21, 2021

(65) Prior Publication Data
US 2022/0000753 A1    Jan. 6, 2022

Related U.S. Application Data

(63) Continuation of application No. 16/075,780, filed as application No. PCT/EP2017/053530 on Feb. 16, 2017, now Pat. No. 11,129,786.

(60) Provisional application No. 62/295,767, filed on Feb. 16, 2016.

(30) Foreign Application Priority Data

Feb. 16, 2016  (EP) ..................... 16155940

(51) Int. Cl.
| | | |
|---|---|---|
| *A61K 8/73* | (2006.01) | |
| *A61K 8/42* | (2006.01) | |
| *A61K 8/44* | (2006.01) | |
| *A61K 8/46* | (2006.01) | |
| *A61Q 5/02* | (2006.01) | |
| *A61Q 5/12* | (2006.01) | |
| *A61Q 19/10* | (2006.01) | |

(52) U.S. Cl.
CPC ............... *A61K 8/737* (2013.01); *A61K 8/42* (2013.01); *A61K 8/442* (2013.01); *A61K 8/466* (2013.01); *A61Q 5/02* (2013.01); *A61Q 5/12* (2013.01); *A61K 2800/30* (2013.01); *A61K 2800/596* (2013.01); *A61Q 19/10* (2013.01)

(58) Field of Classification Search
CPC .......... A61K 8/737; A61K 8/42; A61K 8/466; A61K 8/442; A61K 2800/30; A61K 2800/596; A61Q 5/02; A61Q 5/12; A61Q 19/10

See application file for complete search history.

(56) References Cited

U.S. PATENT DOCUMENTS

2004/0234469 A1*  11/2004  O'Connor .............. C11D 3/382
                                                           424/70.1
2015/0157548 A1    6/2015   De Feij

FOREIGN PATENT DOCUMENTS

| EP | 2196186 A1 | 6/2010 |
|---|---|---|
| WO | 2013150300 A2 | 10/2013 |

\* cited by examiner

*Primary Examiner* — Shirley V Gembeh
(74) *Attorney, Agent, or Firm* — Jarrod N. Raphael

(57) ABSTRACT

The present invention relates to sulfate-free aqueous personal care composition comprising a surfactant system comprising at least one methyl oleoyl taurate, one isethionate and one alkoxylated sulfosuccinate, and from about 0.2 pbw to about 15 pbw of a conditioning agent. It is also directed toward the use of such a composition for washing keratin substrates, in particular the hair or the scalp.

16 Claims, No Drawings

SULFATE-FREE PERSONAL CARE COMPOSITIONS AND METHODS FOR USING SUCH COMPOSITIONS

This application claims priority to U.S. provisional application No. 62/295,767 filed on Feb. 16, 2016 and to European application No. EP16155940 filed on Feb. 16, 2016, the whole content of each of these applications being incorporated herein by reference for all purposes.

The present invention relates to personal care compositions and methods for using such compositions.

At the present time, most of the commercially available personal care compositions are based on sulfate-containing surfactants such as sodium lauryl sulfate, (SLS), ammonium lauryl sulfate (ALS), sodium laureth sulfate (SLES) or ammonium laureth sulfate (ALES). SLS, ALS, SLES and ALES are the most widespread sulfate-containing surfactants used in this field as they are inexpensive and as they exhibit at the same time satisfactory cleansing and foaming properties. Another advantage is that they can be easily thickened by the addition of common salt such as sodium chloride.

However personal care compositions including sulfate-containing surfactants present also significant drawbacks. As a matter of fact sulfate-containing surfactants such as SLS are known to be liable to give rise to tolerance problems, especially on the skin and the eyes. Another drawback of sulfate-containing surfactants is their tendency to strip the skin, scalp or hair of its natural oils, fats or proteins contained at their surface. In the long term the repeated use of personal care compositions including sulfate-containing surfactants may therefore cause irritation to the skin or scalp and/or give damage on hair fibers.

In recent times there is thus an increasing demand for personal care compositions including safe, environment friendly, and/or milder surfactants, and especially for personal care compositions free of sulfate-containing surfactants.

One of the major challenges of formulating sulfate-free personal care compositions lies in the need to maintain mildness, satisfactory cleansing, conditioning and foaming properties without negatively impacting viscosity of the overall composition.

For instance, as far as personal care compositions such as shampoo, shower gel and liquid hand soaps formulations are concerned, an elevated viscosity is necessary for the usage under application conditions. As mentioned previously when sulfate-containing surfactants such as SLS or SLES are present in a composition viscosity can be increased relatively easily by the addition of small amounts of sodium chloride. However, this is generally not the case for anionic surfactants of the acetylated amino acid type, such as methyl cocoyl taurate. Even at very high salt concentrations aqueous solutions are still fluid and not usable for the targeted applications. On the other hand, non-ionic surfactants cannot be thickened at all by the addition of electrolytes. In a sulfate-free surfactant chassis the use of electrolytes such as sodium chloride is therefore not sufficient to provide compositions having an adequate viscosity for use as personal care cleansing compositions. Moreover, compositions involving the use of a thickener of gums, such as xanthan gum, are not always desirable since they have a structuring effect on the gel imparting elastic properties thereto which leads to the formation of thick lumps when drawing the composition out of the bottle.

It is thus an object of the present invention to address the ever increasing demand in the market for personal care compositions that are free of sulfate-containing surfactants without negatively affecting viscosity, foaming properties and conditioning on target area.

One of the aims of the present invention is therefore to provide personal care compositions that exhibit good foaming properties and conditioning on target area and that maintain a satisfactory viscosity, while at the same time being free of sulfate-containing surfactants.

The large majority of known personal care compositions which are free of sulfate-containing surfactants generally need, in order to obtain the foam volume and quality desired by consumers, to contain large amounts of other surfactants.

However, the use of large amounts of surfactants is undesirable of obvious reasons. On the one hand it necessarily increases the overall cost of the compositions. Increasing the amount of surfactants also generally increases on the other hand the risk to lead to tolerance problems.

This is the reason why there is a real need to provide sulfate-free personal care compositions that exhibit good foaming properties and conditioning on target area and that maintain a satisfactory viscosity, without having to use large amounts of surfactants.

The Applicant has now discovered that a personal care composition containing a particular combination of anionic surfactants, one of which is a specific taurate, another one of which is one specific isethionate and another one of which is one alkoxylated sulfosuccinate, makes it possible to achieve the objectives outlined above.

The subject of the invention is thus a sulfate-free aqueous personal care composition comprising:
  i) from about 2 pbw to about 20 pbw of a surfactant system comprising at least:
    a) one methyl oleoyl taurate of formula $R^aCON(CH_3)CH_2CH_2SO_3X^a$, in which $R^a$ is the hydrocarbon radical of oleic acid and $X^a$ is a counterion,
    b) one isethionate of formula $R^bCOOCH_2CH_2SO_3 \ X^b$, in which $R^b$ is a substituted or unsubstituted alkyl, alkenyl, aryl or alkylaryl group having 6 to 30 carbon atoms, and $X^b$ is a counterion, and
    c) one alkoxylated sulfosuccinate, and
  ii) from about 0.2 pbw to about 15 pbw of a conditioning agent.

Surprisingly it has been found that the surfactant mixture used in the compositions according to the invention makes it possible to achieve an acceptable compromise between the following attributes: viscosity of the composition, foaming properties and conditioning on target area, at an equivalent or even decreased overall amount of surfactant and at a reasonable cost.

The presence of a synergic surfactant mixture in the compositions according to the invention was demonstrated by foam measurements and sensorial tests using an expert panel.

The present invention is also directed toward the use of a composition of the invention for washing keratin substrates, in particular the hair or the scalp.

By the expression "sulfate-containing surfactants free composition" or "sulfate-free composition" it is meant that the composition of the invention is devoid of, i.e. does not contain (0%) any anionic surfactant which is a derivative of a sulfate, such as especially sodium lauryl sulfate (SLS), sodium laureth sulfate (SLES), ammonium lauryl sulfate (ALS) or ammonium laureth sulfate (ALES).

For the purposes of the present invention, the term "anionic surfactant which is a derivative of a sulfate" means surfactants comprising at least one anionic group or group that can be ionized into an anionic group, chosen from sulfate functions (—OSO$_3$H or —OSO$_3^-$).

Thus, the following anionic surfactants are preferably not present in the composition according to the invention: salts of alkyl sulfates, of alkylamide sulfates, of alkyl ether sulfates, of alkylamido ether sulfates, of alkylaryl ether sulfates, of monoglyceride sulfates.

By the expression "composition having a satisfactory viscosity" it is meant here a composition that has an apparent viscosity comprised between 1,500 and 50,000 cps, for instance comprised between 2,000 and 30,000 cps, for instance comprised between 3,000 and 25,000 cps. The apparent viscosity of each composition was measured after 24-hours in a temperature-controlled room (21±3° C.), using a Brookfield Viscosimeter Model DV-II+ at 10 RPM, with a RV spindle 4 or 5. The viscosity value was always taken after a stabilization time of 1 min.

According to one embodiment, the composition of the invention has an apparent viscosity of at least 1,500 cps, for instance of at least 2,000 cps.

According to anyone of the invention embodiments, the composition of the invention has an apparent viscosity lower than 50,000 cps, for instance lower than 40,000 cps.

By the expression "foaming properties" it is meant especially here flash foam and foam volume, which are among the main factors affecting the consumer perception about the foam quality. Well-known tests, notably as described in the experimental part, may be used to measure these factors.

By the expression "conditioning on target area" it is meant imparting positive properties to the target area. The target area may be especially a keratinous substrate. As used herein, "keratinous substrates" include, but are not limited to, skin, hair, scalp, lips, eyelashes and nail. Preferably the target area is skin, hair and/or scalp.

For example in the case where the target area is hair "improved conditioning" may cover improved ease of detangling and/or ease of combing.

Ease of detangling may be determined by the measurement of the time required for detangling the hair. The shorter the detangling time is, the easier the hair to detangle is.

Ease of combing may be determined by the measurement of the work required for combing the hair. The lower the combing work is, the easier the hair to comb is.

In the case where the target area is skin, "improved conditioning" may cover improved moisturizing benefits and/or softness.

Conditioning may also be determined by the measurement of the amount of oil deposited on target area. The higher the amount of oil deposited on target area, the higher the resulting conditioning.

Advantageously the compositions of the invention are mild compositions. Mildness may be assessed for instance with the Zein test, which is a conventional method for analyzing the dermal irritation potential of a product.

The terms "consists of or "consisting of in relation to the surfactant system of the composition of the invention are used here to meant that the composition of the invention comprises a surfactant system which is strictly formed of a mixture of the surfactants that are expressly recited, and contains no other surfactants.

The composition of the invention is a personal care composition, preferably a personal care cleansing composition, that is to say a composition aimed to the washing/cleaning and in particular for a body-care application, such as but not limited to a shower gel, a facial cleanser, a body-wash, a liquid hand soap, a shampoo or a cleansing conditioner.

All amounts are in parts by weight (pbw) relative to the total weight of the composition.

For the avoidance of any doubt the amounts of surfactant refer to the actual amount of active surfactant compound present in the composition. In other words, it does not include the residue which may be present as an impurity in a commercially available surfactant mixture.

Should the disclosure of any patents, patent applications, and publications which are incorporated herein by reference conflict with the description of the present application to the extent that it may render a term unclear, the present description shall take precedence A certain combination of particular sulfate-free anionic surfactants is used in the surfactant system of the composition of the present invention.

The composition of the present invention comprises at least one methyl oleoyl taurate of formula R$^a$CON(CH$_3$)CH$_2$CH$_2$SO$_3$X$^a$, in which R$^a$ is the hydrocarbon radical of oleic acid and X$^a$ is a counterion.

The counterion X$^a$ of methyl oleoyl taurate may be an alkali metal ion, alkaline earth metal ion or ammonium ion.

The counterion X$^a$ of methyl oleoyl taurate is typically an alkali metal ion, in particular a sodium ion. It may alternatively be another alkali metal ion, such as potassium or lithium, an alkaline earth metal ion, such as calcium and magnesium, or an optionally substituted ammonium ion, such as an alkyl ammonium having up to 6 aliphatic carbon atoms including isopropylammonium, monoethanolammonium, diethanolammonium and triethanolammonium.

It has been found that the specific use of a methyl oleoyl taurate of the invention, combined with the other specific sulfate-free anionic surfactants of the invention, makes it possible to obtain a better viscosity compared to a composition having no taurate at all, or even compared to a composition including an alternative taurate such as methyl cocoyl taurate.

According to anyone of the invention embodiments, said methyl oleoyl taurate is present in a concentration ranging from 0.1 to 10 pbw relative to the total weight of the composition, for example from 0.5 to 5 pbw, for example from 1 to 3 pbw.

The composition of the present invention also comprises at least one isethionate of formula R$^b$COOCH$_2$CH$_2$SO$_3$ X$^b$, in which R$^b$ is a substituted or unsubstituted alkyl, alkenyl, aryl or alkylaryl group having 6 to 30 carbon atoms, and X$^b$ is a counterion.

According to any one of the invention embodiments, the isethionate may be of formula R$^b$COOCH$_2$CH$_2$SO$_3$ X$^b$, with R$^b$ being an unsubstituted alkyl group having 6 to 30 carbon atoms, for instance 7 to 24 carbon atoms, for instance 7 to 21 carbon atoms.

In some embodiments, the component surfactant of the isethionate type may comprise a mixture of fatty acids to form a mixture of isethionates of formula R$^b$COOCH$_2$CH$_2$SO$_3$ X$^b$, in which R$^b$ may be different.

According to one embodiment, R$^b$ is a residue of a fatty acid.

Fatty acids obtained from natural oils often include mixtures of fatty acids. For example the fatty acid obtained from coconut oil contains a mixture of fatty acids including C$_{12}$ lauric acid, C$_{14}$ myristic acid, C$_{16}$ palmitic acid and C$_8$ caprylic acid.

R$^b$ may include the residue of one or more naturally occurring fatty acids and/or of one or more synthetic fatty acids.

Examples of carboxylic acids from which R$^b$ may be derived residue of include coco acid, butyric acid, hexanoic acid, caproic acid, caprylic acid, capric acid, lauric acid, myristic acid, palmitic acid, palmitoleic acid, stearic acid, oleic acid, linoleic acid, arachidic acid, gadoleic acid, arachidonic acid, eicosapentanoic acid, behinic acid, eruic acid, docosahexanoic acid, lignoceric acid, naturally occurring fatty acids such as those obtained from coconut oil, palm kernel oil, butterfat, palm oil, olive oil, corn oil, linseed oil, peanut oil, fish oil and rapeseed oil; synthetic fatty acids made as chains of a single length or a selected distribution of chain lengths; and mixtures thereof.

Most preferably $R^b$ comprises the residue of lauric acid, that is a saturated fatty acid having 12 carbon atoms, or the residue of mixed fatty acids derived from coconut oil.

The counterion $X^b$ of the isethionate may be an alkali metal ion, alkaline earth metal ion or ammonium ion.

The counterion $X^b$ of the isethionate is typically an alkali metal ion, in particular a sodium ion. It may alternatively be another alkali metal ion, such as potassium or lithium, an alkaline earth metal ion, such as calcium and magnesium, or an optionally substituted ammonium ion, such as an alkyl ammonium having up to 6 aliphatic carbon atoms including isopropylammonium, monoethanolammonium, diethanolammonium and triethanolammonium.

According to anyone of the invention embodiments, said isethionate is present in a concentration ranging from 0.1 to 10 pbw relative to the total weight of the composition, for example from 0.5 to 5 pbw, for example from 1 to 3 pbw.

The composition of the present invention also comprises at least one alkoxylated sulfosuccinate.

According to any one of the invention embodiments, the alkoxylated sulfosuccinate may be an alkoxylated sulfosuccinate of formula $R^c$—O—$(CH_2CH_2O)_n$C(O)$CH_2$CH$(SO_3X^c)CO_2X^c$, wherein n ranges from 1 to 20, $R^c$ is a substituted or unsubstituted alkyl, alkenyl, aryl or alkylaryl group having 6 to 30 carbon atoms, and $X^c$ is a counterion.

According to any one of the invention embodiments, the alkoxylated sulfosuccinate may be an alkoxylated sulfosuccinate of formula $R^c$—O—$(CH_2CH_2O)_n$C(O)$CH_2$CH$(SO_3X^c)CO_2X^c$, wherein n ranges from 2 to 20, $R^c$ is an unsubstituted alkyl group having 6 to 30 carbon atoms, for instance 7 to 24 carbon atoms, for instance 7 to 21 carbon atoms, and $X^c$ is a counterion.

The counterion $X^c$ of the alkoxylated sulfosuccinate may be an alkali metal ion, alkaline earth metal ion or ammonium ion.

The counterion $X^c$ of the alkoxylated sulfosuccinate is typically an alkali metal ion, in particular a sodium ion or an ammonium ion, in particular $NH_4^+$. It may alternatively be another alkali metal ion, such as potassium or lithium, an alkaline earth metal ion, such as calcium and magnesium, or an optionally substituted ammonium ion, such as an alkyl ammonium having up to 6 aliphatic carbon atoms including isopropylammonium, monoethanolammonium, diethanolammonium and triethanolammonium.

According to any one of the invention embodiments, the alkoxylated sulfosuccinate is an alkoxylated sulfosuccinate selected from ammonium and sodium lauryl ether sulfosuccinates.

According to anyone of the invention embodiments, said alkoxylated sulfosuccinate is present in a concentration ranging from 0.1 to 10 pbw relative to the total weight of the composition, for example from 1 to 8 pbw, for example from 2 to 6 pbw.

Among the various sulfate-free anionic surfactants, the alkoxylated sulfosuccinate of the invention may be advantageously present in the greatest relative amount, compared to the methyl oleoyl taurate and to the isethionate of the invention.

In other words, the amount of alkoxylated sulfosuccinate of the invention present in the final composition may be greater than the amount of the methyl oleoyl taurate of the invention and the amount of alkoxylated sulfosuccinate of the invention present in the final composition may be also greater than the amount of isethionate of the invention.

According to any one of the invention embodiments, the weight ratio of alkoxylated sulfosuccinate (c) to methyl oleoyl taurate (a) is greater than or equal to 1, preferably is greater than 1, in a composition of the invention, based on the weight percent of each surfactant in the final composition.

According to any one of the invention embodiments, the weight ratio of alkoxylated sulfosuccinate (c) to isethionate (b) is greater than or equal to 1, preferably is greater than 1, in a composition of the invention, based on the weight percent of each surfactant in the final composition.

According to any one of the invention embodiments, the concentration in the methyl oleoyl taurate (a), isethionate (b) and alkoxylated sulfosuccinate (c) in a composition of the invention may range from 1 to 20 pbw, for instance from 2 to 15 pbw, for instance from 2 to 10 pbw, relative to the total weight of the composition.

According to any one of the invention embodiments the surfactant system may comprise as optional component additional sulfate-free surfactants, which can be selected amongst a monoalkyl sulfosuccinate of formula $R^cO_2CCH_2CH(SO_3X^c)CO_2X^c$, an amido-MEA sulfosuccinate of formula $R^cCONHCH_2CH_2O_2CCH_2CH(SO_3X^c)CO_2X^c$ or an amido-MIPA sulfosuccinate of formula $R^cCONH(CH_2)CH(CH_3)(SO_3X^c)CO_2X^c$, with $R^c$ and $X^c$ being as defined previously.

According to any one of the invention embodiments the surfactant system may comprise as optional component additional sulfate-free surfactants, which can be selected amongst amphoteric, zwitterionic or non ionic surfactants.

In particular, the composition of the present invention may further comprise at least one amphoteric or zwitterionic surfactant chosen from (i) amphoacetates and diamphoacetates, (ii) sultaines and (iii) alkylbetaines.

The composition of the invention may comprise for example an amphoacetate of formula:

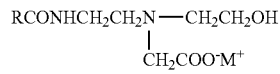

where R is an aliphatic group of 8 to 22 carbon atoms and M is a cation such as sodium, potassium, ammonium or substituted ammonium.

The composition of the invention may comprise for example a diamphoacetates of formula:

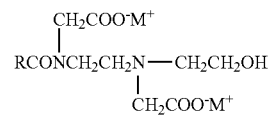

where R is an aliphatic group of 8 to 22 carbon atoms and M is a cation such as sodium, potassium, ammonium or substituted ammonium.

In another embodiment, the composition of the invention comprises (ii) at least one sultaine.

The composition of the invention may comprise for example a sultaine of formula:

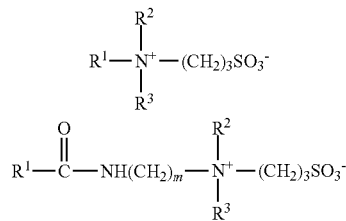

where m is 2 or 3, or variants of these in which —$(CH_2)_3SO_3^-$ is replaced by:

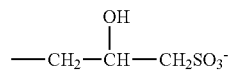

where $R^1$ is a substituted or unsubstituted alkyl or alkenyl group having 7 to 22 carbon atoms, and $R^2$ and $R^3$ are each independently alkyl, hydroxyalkyl or carboxyalkyl of 1 to 6 carbon atoms.

In another embodiment, the composition of the invention comprises (iii) at least one alkylbetaine.

The composition of the invention may comprise for example an alkylbetaine of formula:

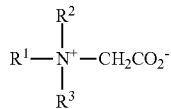

where $R^1$ is a substituted or unsubstituted alkyl or alkenyl group having 7 to 22 carbon atoms, and $R^2$ and $R^3$ are each independently alkyl, hydroxyalkyl or carboxyalkyl of 1 to 6 carbon atoms.

$R^1$ may, in particular, be a mixture of $C_{12}$ and $C_{14}$ alkyl groups derived from coconut so that at least half, preferably at least three quarters, of the groups $R^1$ has 10 to 14 carbon atoms. $R^2$ and $R^3$ are preferably methyl.

If present, the amount of amphoteric or zwitterionic surfactant of the invention present in the final composition may be greater than the amount of the methyl oleoyl taurate of the invention and the amount of amphoteric or zwitterionic surfactant of the invention present in the final composition may be also greater than the amount of isethionate of the invention.

According to any one of the invention embodiments, the composition of the present invention comprises at least one amphoteric or zwitterionic surfactant and the weight ratio of amphoteric or zwitterionic surfactant to methyl oleoyl taurate (a) is greater than or equal to 1, preferably is greater than 1, in a composition of the invention, based on the weight percent of each surfactant in the final composition.

According to any one of the invention embodiments, the composition of the present invention comprises at least one amphoteric or zwitterionic surfactant and the weight ratio of amphoteric or zwitterionic surfactant to isethionate (b) is greater than or equal to 1, preferably is greater than 1, in a composition of the invention, based on the weight percent of each surfactant in the final composition.

In one specific embodiment, the composition of the present invention may further comprise one or more nonionic surfactants selected from alkanolamide surfactants and glycoside surfactants.

Suitable alkanolamide surfactants are known compounds and include, for example, acetamide MEA, cocamide DEA, cocamide MEA, cocamide methyl MEA, cocamide MIPA, hydroxystearamide MEA, PEG-5 cocamide MEA, lactamide MEA, lauramide MEA and lauramide DEA, preferably cocamide MIPA or cocamide methyl MEA.

Suitable glycoside surfactants are known compounds and include, for example, ($C_4$-$C_{22}$)alkylhexosides, such as butylglucoside, nonylglucoside, decylglucoside, dodecyl glucoside, hex adecylglucoside, octadecylglucoside, cocoglucoside, laurylglucoside, caproyl ethyl glucoside, caprylyl/capryl glucoside, caprylyl gluco side, ($C_4$-$C_{22}$) alkylpolyhexosides, such as butylpolyglucosides, nonylpolyglucosides, decylpolyglucosides, tetradecylpolyglucosides, hexadecylpolyglucosides, erucylpolyglucosides, ($C_4$-$C_{22}$)alkylpentosides, such as nonylarabinosides, decylarabinoside, hexadecylarabinoside, octylxyloside, nonylxyloside, decylxyloside, hexadecylxyloside, erucylxyloside, and ($C_4$-$C_{22}$)alkylpolypentosides, such as butylpolyarabinosides, nonylpolyarabinosides, decylpolyarabinosides, hex adecylpol yarabinosides, octadecylpolyarabinosides, erucylpolyarabinosides, butylpolyxylosides, nonylpolyxylosides, decylpolyxylosides, octadecylpolyxylosides, and erucylpolyxylosides, butylpoly(arabino-co-xylo)sides, nonylpoly(arabino-co-xylo)sides, decylpoly(arabino-co-xylo) sides, hexadecylpoly(arabino-co-xylo)sides, octadecylpoly (arabino-co-xylo)sides, erucylpoly(arabino-co-xylo)sides, and mixtures of any of such compounds, wherein the terminology "poly(arbino-co-xylo)side" denotes a copolymeric chain of monomeric residues of arabinose and xylose. Preferably the glycoside surfactant is decylglucoside.

According to a particular embodiment of the invention, said optional additional sulfate-free surfactants selected amongst amphoteric, zwitterionic or non ionic surfactants are incorporated in amounts varying between 0.5 and 5 pbw relative to the total weight of the composition.

According to any one of the invention embodiments, the composition of the invention further comprises of at least one amphoteric or zwitterionic surfactant chosen from amphoacetates and diamphoacetates, preferably a lauroamphoacetate, and at least one nonionic surfactant chosen from alkanolamide surfactants and glycoside surfactants, and does not comprise any additional sulfate-free surfactants.

The surfactant system in the composition of the invention may consist of one methyl oleoyl taurate of formula $R^aCON(CH_3)CH_2CH_2SO_3X^a$, in which $R^a$ is the hydrocarbon radical of oleic acid and $X^a$ is a counterion, one isethionate of formula $R^bCOOCH_2CH_2SO_3$ $X^b$, in which $R^b$ is a substituted or unsubstituted alkyl, alkenyl, aryl or alkylaryl group having 6 to 30 carbon atoms, and $X^b$ is a counterion, one alkoxylated sulfosuccinate, one amphoteric or zwitterionic surfactant chosen from amphoacetates and diamphoacetates and one nonionic surfactant chosen from alkanolamide surfactants and glycoside surfactants.

According to any one of the invention embodiments, the total amount of surfactants in a composition of the invention ranges from 5 to 15 pbw, relative to the total weight of the composition.

The weight ratio of anionic surfactants to amphoteric surfactants may typically range from 1:10 to 10:1.

According to any one of the invention embodiments, the composition of the invention may comprise an anionic-rich surfactant chassis, that is to say a surfactant chassis in which the ratio of anionic surfactants to amphoteric surfactants is greater than 1, for instance greater than 2.

In another embodiment of the invention, the composition of the invention may comprise an amphoteric-rich surfactant chassis, that is to say a surfactant chassis in which the ratio of amphoteric surfactants to anionic surfactants is greater than 1, for instance greater than 2.

The composition of the invention further comprises a conditioning agent, especially a cationic or ampholytic conditioning agent. Such agents can assist in oil deposition. They might also provide some conditioning effects. They can for example enhance the appearance and feel of hair, increase hair body or suppleness, facilitate combing and styling, improve gloss or sheen and improve the texture of hair that has been damaged by chemical or physical action. They can provide anti-static effect, in altering the static electrical properties of hair.

According to any one of the invention embodiments the conditioning agent may be a cationic cellulose.

Cationic cellulose is available from Amerchol Corp. (Edison, N.J., USA) in their Polymer JR (trade mark) and LR (trade mark) series of polymers, as salts of hydroxyethyl cellulose reacted with trimethyl ammonium substituted epoxide, referred to in the industry (CTFA) as Polyquaternium 10. Another type of cationic cellulose includes the polymeric quaternary ammonium salts of hydroxyethyl cellulose reacted with lauryl dimethyl ammonium-substituted epoxide, referred to in the industry (CTFA) as Polyquaternium 24. These materials are available from Amerchol Corp. (Edison, N.J., USA) under the tradename Polymer LM-200.

In another embodiment, the conditioning agent may be a cationic polysaccharide polymer, especially a cationic guar gum derivative, such as guar hydroxypropyltrimonium chloride (Commercially available from Rhodia in their JAGUAR trademark series). Examples are JAGUAR C13S, which has a low degree of substitution of the cationic groups and high viscosity, JAGUAR C17 (high degree of substitution, high viscosity), and JAGUAR 162 which is a high transparency, medium viscosity guar having a low degree of substitution. Mention may be also made of JAGUAR C14S, JAGUAR Excel, JAGUAR C500, JAGUAR LS and JAGUAR Optima.

Particularly preferred cationic polymers are JAGUAR C162, JAGUAR LS and JAGUAR Optima.

Other cationic or ampholytic conditioning agent known in the art may be used provided that they are compatible with the inventive composition.

Mention may be made especially of synthetic cationic polymers (for example polymers comprising units having a quaternary ammonium group or a tertiary ammonium group, and optionally neutral units) and of synthetic ampholytic copolymers (for example polymers comprising units having a quaternary ammonium group or a tertiary ammonium group, units having an anionic (usually acidic) group and optionally neutral units).

Conditioning agents are known by the one skilled in the art. Examples of typical conditioning agents include (INCI names):

Polyquaternium-1; Polyquaternium-2; Polyquaternium-4; Polyquaternium-5; Polyquaternium-6; Polyquaternium-7; Polyquaternium-8; Polyquaternium-9; Polyquaternium-10; Polyquaternium-11; Polyquaternium-12; Polyquaternium-13; Polyquaternium-14; Polyquaternium-15; Polyquaternium-16; Polyquaternium-17; Polyquaternium-18; Polyquaternium-19; Polyquaternium-20; Polyquaternium-22; Polyquaternium-24; Polyquaternium-27; Polyquaternium-28; Polyquaternium-29; Polyquaternium-30; Polyquaternium-31; Polyquaternium-32; Polyquaternium-33; Polyquaternium-34 Polyquaternium-35; Polyquaternium-36; Polyquaternium-37; Polyquaternium-39; Polyquaternium-43; Polyquaternium-44; Polyquaternium-45; Polyquaternium-46; Polyquaternium-47; Polyquaternium-48; Polyquaternium-49; Polyquaternium-50; Polyquaternium-52; Polyquaternium-53; Polyquaternium-54; Polyquaternium-55; Polyquaternium-56; Polyquaternium-57; Polyquaternium-58; Polyquaternium-59; Polyquaternium-60; Polyquaternium-63; Polyquaternium-64; Polyquaternium-65; Polyquaternium-66; Polyquaternium-67; Polyquaternium-70; Polyquaternium-73; Polyquaternium-74; Polyquaternium-75; Polyquaternium-76; Polyquaternium-85; Polyquaternium-86; Polybeta-Alanine; Polyepsilon-Lysine; Polylysine; PEG-8/SMDI Copolymer; PPG-12/SMDI Copolymer; PPG-51/SMDI Copolymer; PPG-7/Succinic Acid Copolymer; IPDI/PEG-15 Cocamine Copolymer; IPDI/PEG-15 Cocamine Copolymer Dimer Dilinoleate; IPDI/PEG-15 Soyamine Copolymer; IPDI/PEG-15 Soyamine Oxide Copolymer; IPDI/PEG-15 Soyethonium Ethosulfate Copolymer; Polyquaternium-4/Hydroxypropyl Starch Copolymer; Cassia Hydroxypropyltrimonium Chloride; Chitosan Hydroxypropyltrimonium Chloride; Dextran Hydroxypropyltrimonium Chloride; Galactoarabinan Hydroxypropyltrimonium Chloride; *Ginseng* Hydroxypropyltrimonium Chloride; Guar Hydroxypropyltrimonium Chloride; Hydroxypropyl Guar Hydroxypropyltrimonium Chloride; Locust Bean Hydroxypropyltrimonium Chloride; Starch Hydroxypropyltrimonium Chlorid; Hydroxypropyltrimonium Hydrolyzed Wheat Starch; Hydroxypropyltrimonium Hydrolyzed Corn Starch; Hydroxypropyl Oxidized Starch PG-Trimonium Chloride; Tamarindus Indica Hydroxypropyltrimonium Chloride; Polyacrylamidopropyltrimonium Chloride; Polymethacrylamidopropyltrimonium Chloride; Polymethacrylamidopropyltrimonium Methosulfate; Propyltrimoniumchloride Methacrylamide/Dimethylacrylamide Copolymer; Acrylamide/Ethalkonium Chloride Acrylate Copolymer; Acrylamide/Ethyltrimonium Chloride Acrylate/Ethalkonium Chloride Acrylate Copolymer; Acrylates/Carbamate Copolymer; Adipic Acid/Methyl DEA Crosspolymer; Diethylene Glycol/DMAP Acrylamide/PEG-180/HDI Copolymer; Dihydroxyethyl Tallowamine/IPDI Copolymer; Dimethylamine/Ethylenediamine/Epichlorohydrin Copolymer; HEMA Glucoside/Ethylmethacrylate Trimonium Chloride Copolymer; Hydrolyzed Wheat Protein/PEG-20 Acetate Copolymer; Hydrolyzed Wheat Protein/PVP Crosspolymer; Ethyltrimonium Chloride Methacrylate/Hydroxyethylacrylamide Copolymer.

The amount of cationic or ampholytic conditioning agent in the compositions can preferably be in the range from 0.1 to 10 pbw, particularly preferably in the range from 0.2 to 5 pbw, and especially preferably in the range from 0.5 to 2.5 pbw, based on the compositions.

According to any one of the invention embodiments, the composition of the present invention comprise, based on 100 pbw of such composition, from 0 to less than 2 pbw of one isethionate of formula (I'):

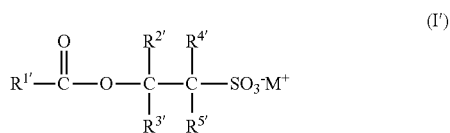

(I')

wherein $R^{1'}$ represents a $C_{4-30}$ substituted or unsubstituted hydrocarbyl group; each of $R^{2'}$, $R^{3'}$, $R^{4'}$ and $R^{5'}$ independently represents a hydrogen atom or a $C_{1-4}$ alkyl group and wherein at least one of $R^{2'}$, $R^{3'}$, $R^{4'}$ and $R^{5'}$ is not hydrogen, and $M^+$ represents a cation.

Typical isethionates of formula (I') are sodium lauryl methyl isethionate and sodium cocoyl methyl isethionate.

Isethionates of formula (I') are not desirable components of the composition of the present invention.

More typically the composition of the present invention comprise, based on 100 pbw of such composition, from 0 to less than 1 pbw of isethionates of formula (I') and even substantially no isethionate of formula (I'), i.e. from 0 to less than 0.1 pbw isethionate of formula (I') per 100 pbw of the composition, more typically no isethionate of formula (I'), i.e. 0 pbw isethionate of formula (I') per 100 pbw of the composition.

According to any one of the invention embodiments, the composition of the present invention each comprise, based on 100 pbw of such composition, from 0 to less than 2 pbw of one amidobetaine, such as for example cocamidopropyl betaine.

More typically the composition of the present invention each comprise, based on 100 pbw of such composition, from 0 to less than 1 pbw of amidobetaine (for example cocamidopropyl betaine), and even substantially no amidobetaine, i.e. from 0 to less than 0.1 pbw amidobetaine per 100 pbw of the composition, more typically no amidobetaine, i.e. 0 pbw amidobetaine per 100 pbw of the composition.

According to any one of the invention embodiments, the composition of the present invention may further comprise an electrolyte.

By the term "electrolyte" we mean here ionic salt totally soluble in the composition at the concentrations used.

According to any one of the invention embodiments, the electrolyte of any composition according to the invention can be selected from the group of alkali, and ammonium salts. In particular such electrolyte can be an alkali salt. As non limiting examples, one may cite electrolyte such as NaCl or KCl.

According to any one of the invention embodiments, the electrolyte is present in the composition in a concentration of about 0.2 to 3 pbw relative to the weight of the composition, for instance in a concentration lower than 2.5 pbw.

The composition of the invention may further comprise additional optional ingredients which may bring specific benefits for the intended use. Such optional ingredients may include colorants, pearlescent agents, emollients, hydrating agents, opacifiers, preservatives and pH adjusters. The skilled person is able to select according to general knowledge in the art of formulating personal care compositions such as shampoos, shower gels and liquid hand soaps, and the vast literature there-related, appropriate such optional ingredients for application purposes.

In one embodiment, the composition of the present invention further comprises one or more benefit agents, such as emollients, moisturizers, conditioners, skin conditioners, or hair conditioners such as silicones such as volatile silicones, gums or oils, or non-amino silicones and mixtures thereof, mineral oils, vegetable oils, including arachis oil, castor oil, cocoa butter, coconut oil, corn oil, cotton seed oil, olive oil, palm kernel oil, rapeseed oil, safflower seed oil, sesame seed oil and soybean oil, esters, including butyl myristate, cetyl palmitate, decyloleate, glyceryl laurate, glyceryl ricinoleate, glyceryl stearate, glyceryl isostearate, hexyl laurate, isobutyl palmitate, isocetyl stearate, isopropyl isostearate, isopropyl laurate, isopropyl linoleate, isopropyl myristate, isopropyl palmitate, isopropyl stearate, propylene glycol monolaurate, propylene glycol ricinoleate, propylene glycol stearate, and propylene glycol isostearate, animal fats, including acetylated lanolin alcohols, lanolin, lard, mink oil and tallow, and fatty acids and alcohols, including behenic acid, palmitic acid, stearic acid, behenyl alcohol, cetyl alcohol, eicosanyl alcohol and isocetyl alcohol; vitamins or their derivatives, such as vitamin B complex, including thiamine, nicotinic acid, biotin, pantothenic acid, choline, riboflavin, vitamin B6, vitamin B12, pyridoxine, inositol, carnitine, vitamins A, C, D, E, K and their derivatives, such as vitamin A palmitate, and pro-vitamins, e.g., panthenol (pro vitamin B5), panthenol triacetate and mixtures thereof; antioxidants; free-radical scavengers; abrasives, natural or synthetic; dyes; hair coloring agents; bleaching agents; hair bleaching agents; UV absorbers, such as benzophenone, bornelone, PABA (Para Amino Benzoic Acid), butyl PABA, cinnamidopropyl trimethyl ammonium chloride, disodium distyrylbiphenyl disulfonate, potassium methoxycinnamate; anti-UV agents, such as butyl methoxydibenzoylmethane, octyl methoxycinnamate, oxybenzone, octocrylene, octyl salicylate, phenylbenzimidazole sulfonic acid, ethyl hydroxypropyl aminobenzoate, menthyl anthranilate, aminobenzoic acid, cinoxate, diethanolamine methoxycinnamate, glyceryl aminobenzoate, titanium dioxide, zinc oxide, oxybenzone, octyl dimethyl PABA (padimate O), red petrolatum; antimicrobial agents; antibacterial agents, such as bacitracin, erythromycin, triclosan, neomycin, tetracycline, chlortetracycline, benzethonium chloride, phenol, parachlorometa xylenol (PCMX), triclocarban (TCC), chlorhexidine gluconate (CHG), zinc pyrithione, selenium sulfide; antifungal agents; melanin regulators; tanning accelerators; depigmenting agents, such as retinoids such as retinol, kojic acid and its derivatives such as, for example, kojic dipalmitate, hydroquinone and its derivatives such as arbutin, transexamic acid, vitamins such as niacin, vitamin C and its derivatives, azelaic acid, placertia, licorice, extracts such as chamomile and green tea, where retinol, kojic acid, and hydroquinone are preferred; skin lightening agents such as hydroquinone, catechol and its derivatives, ascorbic acid and its derivatives; skin-coloring agents, such as dihydroxyacetone; liporegulators; weight-reduction agents; anti-acne agents; antiseborrhoeic agents; anti-ageing agents; anti-wrinkle agents; keratolytic agents; anti-inflammatory agents; anti-acne agents, such as tretinoin, isotretinoin, motretinide, adapalene, tazarotene, azelaic acid, retinol, salicylic acid, benzoyl peroxide, resorcinol, antibiotics such as tetracycline and isomers thereof, erythromycin, anti-inflammatory agents such as ibuprofen, naproxen, hetprofen, botanical extracts such as alnus, arnica, artemisia capillaris, asiasarum root, calendula, chamomile. Cnidium, comfrey, fennel, galla rhois, hawthorn, houttuynia, hypericum, jujube, kiwi, licorice, magnolia, olive, peppermint, philodendron, salvia, sasa albomarginata, imidazoles such as ketoconazole and elubiol, those anti-acne agents described in Gollnick, H. et al. 196 (1) Dermatology Sebaceous Glands, Acne and Related Disorders, 119-157 (1998), which is incorporated by reference herein to the extent that it is not inconsistent with the present application; refreshing agents; cicatrizing agents; vascular-protection agents; agents for the reduction of dandruff, seborrheic dermatitis, or psoriasis, such as zinc pyrithione, shale oil and derivatives thereof such as sulfonated shale oil, selenium sulfide, sulfur, salicylic acid, coal tar, povidone-iodine, imidazoles such as ketoconazole, dichlorophenyl imidazolodioxalan, clotrimazole, itraconazole, miconazole, climbazole, tioconazole, sulconazole, butoconazole, fluconazole, miconazolenitrite and any possible stereo isomers and derivatives thereof such as anthralin, piroctone olamine (Octopirox), selenium sulfide, ciclopirox olamine, anti-psoriasis agents such as vitamin D analogs, e.g. calcipotriol, calcitriol, and tacaleitrol, vitamin A analogs such as esters of vitamin A including vitamin A palmitate, retinoids, retinols, and retinoic acid, corticosteroids such as hydrocortisone, clobetasone, butyrate, clobetasol propionate; antiperspirants or deodorants, such as aluminum chlorohydrates, aluminum zirconium chlorohydrates; immunomodulators; nourishing agents; depilating agents, such as calcium thioglycolate, magnesium thioglycolate, potassium thioglycolate, strontium thioglycolate; agents for combating hair loss; reducing agents for permanent-waving; reflectants, such as mica, alumina, calcium silicate, glycol dioleate, glycol distearate, silica, sodium magnesium fluorosilicate; essential oils and fragrances.

In one embodiment, the composition of the present invention comprises a benefit agent selected from insoluble or partially insoluble ingredients such as moisturizers or conditioners, hair coloring agents, anti-UV agents, anti-wrinkle agents, fragrances or essential oils, skin-coloring agents, anti-dandruff agents, and provides enhanced deposition of such benefit agent on the substrate, ex. Hair and/or skin or fabric or counter top or plant leaves.

In one embodiment, the personal care composition of the present invention further comprises from about 0.1 to about 50 pbw, more typically from about 0.3 to about 25 pbw, and still more typically from about 0.5 to 10 pbw, of one or more benefit agents.

The composition according to the present invention may optionally further comprise other ingredients, such as, for example, preservatives such as benzyl alcohol, methyl paraben, propyl paraben, imidazolidinyl urea, sodium benzoate, potassium sorbate, salicylic acid, methylchloroisothiazolinone and methylisothiazolinone, thickeners such as high molecular weight crosslinked polyacrylic acid (carbomer), PEG diester of stearic acid and the like, and viscosity modifiers such as block polymers of ethylene oxide and propylene oxide, electrolytes, such as sodium chloride, sodium sulfate, and polyvinyl alcohol, pH adjusting agents such as citric acid, succinic acid, phosphoric acid, sodium hydroxide, and sodium carbonate, perfumes, dyes, and sequestering agents, such as disodium ethylenediamine tetra-acetate. In general, personal care compositions may optionally comprise, based on 100 pbw of the personal care composition and independently for each such ingredient, up to about 10 pbw, preferably from 0.5 pbw to about 5.0 pbw, of such other ingredients, depending on the desired properties of the personal care composition.

In general, a composition of the present invention may optionally comprise, based on 100 pbw of the personal care composition and independently for each such ingredient, up to about 15 pbw, preferably from 0.5 pbw to about 10 pbw, of such other ingredients, depending on the desired properties of the composition.

The composition of the present invention is used in a manner know in the art, for example, in the case of a cleanser or shampoo, by application of the cleanser or shampoo to the skin and/or hair and optionally rinsing the cleanser or shampoo off of the skin and/or hair with water.

According to any one of the invention embodiments, the composition of the invention may have a pH comprised between 4 and 11.

According to any one of the invention embodiments, the composition of the invention may be prepared using a concentrated flowable surfactant composition.

The invention is also directed toward concentrates that are suitable to prepare a composition of the invention.

Concentrates including a mixture of surfactants and/or conditioning agents are advantageous as their use would reduce the need to transport a plurality of individual components.

Personal care compositions are usually prepared by mixing individual surfactants and conditioning agents. These components may be supplied as concentrated solutions which are diluted and/or and combined in appropriate ratios by the formulator. The invention covers any surfactant concentrate to be used as component ingredient to prepare a composition of the invention, and especially to surfactant concentrates containing limited levels of water (more advantageous from a cost and environmental perspective).

EXAMPLES

The invention will now be described in further detail by way of the following non limiting examples, wherein the abbreviations have the usual meaning in the art. The temperatures are indicated in degrees centigrade (° C.) and the other parameters in the respective current units. Water amount indicated as "q.s." are intended to be "the amount required to complete to 100%".

Viscosity Measurement

The viscosity of each composition was measured after 24-hours in a temperature-controlled room (21±3° C.), using a Brookfield Viscosimeter Model DV-II+ at 10 RPM, with a RV spindle 4 or 5. The viscosity value was always taken after a stabilization time of 1 min.

Example 1

The following sulfate-free shampoo compositions were prepared.

The starting materials used are identified by the INCI names and/or by the commercial references. All ingredients are expressed by weight percent of the total formulation and as level of active ingredients.

|  | Comparative Formulation 1 | Formulation 1 | Comparative Formulation 2 | Formulation 2 |
|---|---|---|---|---|
| Mackanate ® EL (Disodium Laureth Sulfosuccinate) | 6.0 | 6.0 | 6.0 | 6.0 |
| Mackam ® CBS-50G (Cocamidopropyl Hydroxysultain) | 4.0 | 4.0 | — | — |

-continued

|  | Comparative Formulation 1 | Formulation 1 | Comparative Formulation 2 | Formulation 2 |
|---|---|---|---|---|
| Miranol ® Ultra L32 (Sodium Lauroamphoacetate) | — | — | 4.0 | 4.0 |
| Pureact ® I-78C Sodium Cocoyl Tsethionate) | 2.0 | 2.0 | 2.0 | 2.0 |
| Geropon ® T-77 (Sodium Methyl Oleoyl Taurate) | — | 1.8 | — | 1.8 |
| Geropon ® TC-42 LQ (Sodium Methyl Cocoyl Taurate) | 1.8 | — | 1.8 | — |
| Mackamide ® CPA (Cocamide MIPA) | 1.5 | 1.5 | 1.5 | 1.5 |
| sodium chloride | 1.63 | 1.63 | 1.3 | 1.3 |
| Jaguar ® LS (Hydroxypropyl Guar hydroxypropyltrimonium chloride) | 0.3 | 0.3 | 0.3 | 0.3 |
| Citric acid solution (50%) | q.s | q.s | q.s | q.s |
| Kathon ® CG (Methylchloroisothiazolinone, Methylisothiazolinone) | 0.05 | 0.05 | 0.05 | 0.05 |
| De-ionized water | Up to 100 | Up to 100 | Up to 100 | Up to 100 |
| pH | 5.4 | 5.4 | 6.0 | 6.0 |
| Brookfield Viscosity @ 10 RPM, RV spindle 4 or 5 (mPa · s) | <500 | Between 2,000 and 5,000 | <1,000 | Between 26,000 and 29,000 |

Formulation Procedure

Add 24 parts of de-ionized water in a tared beaker A under continuous stirring and heat at 65° C. Add Mackamide® CPA and mix at 100 RPM. After 10 minutes, add Pureact®I-78C and let under stirring during 30 minutes. Stop heating and let the mixture under stirring until it comes back at 30° C. If necessary, compensate for water loss that has occurred during heating step.

In another vessel, charge 26 parts of de-ionized water. Add Jaguar LS in the vessel and add a few drops of citric acid solution (50%) under stirring, until the solution becomes clear. Add Miranol® Ultra L32 (or Mackam® CBS-50G) under stirring, followed by Mackanate® EL. Add the pre-mix of beaker A into the main vessel under continuous stirring at 100 RPM during 10 minutes. Add Geropon® T-77 in the form of a 25 wt % dilution in water (or Geropon TC-42LQ) and stir during 10 minutes. Adjust pH between 5.0 and 6.0 with a 50% solution of citric acid, add Kathon®CG and add the required amount of sodium chloride under stirring. Add de-ionized water up to 100 parts.

Performances

Formulation 1, which includes the particular combination of anionic surfactants in accordance with the invention, is a cleansing composition displaying acceptable viscosity (above 1,500 cps) contrary to Comparative Formulation 1.

Formulation 2, which includes the particular combination of anionic surfactants in accordance with the invention too, is an alternative cleansing composition which displays also acceptable viscosity (between 1,500 and 50,000 cps), contrary to Comparative Formulation 2.

Sensorial tests confirmed that Formulations 1 and 2 of the invention exhibit at the same time good foaming properties and good conditioning.

These examples illustrate that the particular combination of surfactants required according to the invention, namely the combination of a methyl oleoyl taurate with one isethionate of the invention and with one alkoxylated sulfosuccinate, is critical to achieve good foaming and conditioning properties, while maintaining an acceptable viscosity in a sulfate-free surfactant chassis.

Example 2

The following sulfate-free shampoo compositions were prepared.

The starting materials used are identified by the INCI names and/or by the commercial references. All ingredients are expressed by weight percent of the total formulation and as level of active ingredients.

|  | Comparative Formulation 3 | Formulation 3 |
|---|---|---|
| Mackanate ® EL (Disodium Laureth Sulfosuccinate) | — | 6.0 |
| Mackanate LO 100 (Disodium Lauryl Sulfosuccinate) | 6.0 | — |
| Mackam ® CBS-50G (Cocamidopropyl Hydroxysultain) | 4.0 | 4.0 |
| Pureact ® I-78C (Sodium Cocoyl Isethionate) | 2.0 | 2.0 |
| Geropon ® T-77 (Sodium Methyl Oleoyl Taurate) | 1.8 | 1.8 |
| Mackamide ® CPA (Cocamide MIPA) | 1.5 | 1.5 |
| sodium chloride | 2.0 | 2.6 |
| Jaguar ® LS (Hydroxypropyl guar Hydroxypropyltrimonium chloride) | 0.4 | 0.4 |

-continued

|  | Comparative Formulation 3 | Formulation 3 |
|---|---|---|
| Citric acid solution (50%) | q. s | q. s |
| De-ionized water | Up to 100 | Up to 100 |
| pH | 5.3 | 5.4 |
| Brookfield Viscosity @10 RPM, RV spindle 4 or 5 (mPa · s) | Between 7,000 and 10,000 | Between 7,000 and 10,000 |

Formulation Procedure

Add 27 parts of de-ionized water in a tared beaker A under continuous stirring and heat at 65° C. Add Mackamide® CPA and mix at 100 RPM. After 10 minutes, add Pureact®I-78C. After 5 minutes add Geropon® T-77 and let under stirring during 30 minutes. Stop heating and let the mixture under stirring until it comes back at 30° C. If necessary, compensate for water loss that has occurred during heating step.

In another vessel, charge 30 parts of de-ionized water. Add Jaguar LS in the vessel and adjust pH at 5.5 with a 50% solution of citric acid, under stirring, until the solution becomes clear. Add Mackam® CBS-50G under stirring, followed by Mackanate® EL (resp. Mackanate® LO 100). Add the pre-mix of beaker A into the main vessel under continuous stirring at 100 RPM during 10 minutes. Add sodium chloride up to achieve a targeted viscosity of [7,000-10,000 mPa·s] at 10 RPM and adjust pH at 5.5±0.2 with a 50% solution of citric acid under continuous stirring. Add de-ionized water up to 100 parts.

Performances

Viscosity of each formulation has been adjusted with added salt (sodium chloride) to yield formulations having a similar viscosity within a satisfactory range (between 7,000 and 10,000 cps).

In this viscosity range the performances of Formulation 3 (which includes the particular combination of anionic surfactants including an alkoxylated sulfosuccinate in accordance with the invention) have been compared to the performances of Comparative Formulation 3, in terms of sensorial assessment on hair tresses, foam volume and flash foam, according to the following methodologies.

Sensorial Assessment on Hair Tresses

Flat Calibrated tresses of bleached Caucasian hair, weighing about 10 grams, length of hair: 21 cm below clip and 3 cm width were used. They were purchased from Kerling International Haarfabik GmbH, Donaustr. 7, D-71522 Backnang-Waldrems in Germany. Sensorial analysis was performed by a trained expert panellist, following the standardized protocol described below.

Prior to being actually shampooed, the hair tresses were first cleansed with a 10% active sodium laureth sulfate (SLES) solution. Each hair tress was then wetted under flowing tap water (controlled flow 1100 mL+/−40 mL per 10 sec) at controlled temperature (36.5° C.±1° C.) during 1 minute. 1 ml of shampoo formulation was applied over the entire length of the hair tress and foam was produced by massaging the hair tress from the top to the bottom during 1 min 30 sec with one's hand. The speed at which the foam forms after 15 seconds (so-called "flash-foam") was scored (a score of 1 corresponds to a very slow-forming foam; a score of 2, a slow-forming foam; a score of 3, a medium rapid forming foam; a score of 4, a rapid forming foam; a score of 5 a very rapid forming foam).

The foam generated in the hands and on hair tress was then collected in a conic beaker of 250 mL. The amount of foam was assessed and the foam quality attributes were noted (whiteness, density, richness). Then the hair tress was rinsed during 1 min 15 sec, under flowing tap water at controlled flow, with gentle squeezing of the hair tress from roots to tips with the fingers. After rinsing, the excess water was removed by squeezing the hair tress with two fingers, and the time necessary to detangle the hair tress with a wide-tooth comb was monitored.

Sensorial analysis on bleached hair tresses were performed by one expert panelist. Results were the following:

|  | Comparative Formulation 3 | Formulation 3 |
|---|---|---|
| flash foam [score 1 (very low)-5 (very high)] | 2.5 | 3.0 |
| Foam volume (ml) | 30 ml | 50 ml |
| Delangling lime | 6 min 12 sec | 4 min 09 sec |

Formulation 3 (which includes the particular combination of anionic surfactants including an alkoxylated sulfosuccinate in accordance with the invention) exhibits overall better performances (in terms of speed of foam formation, foam volume and time necessary to achieve hair tress detangling) compared to Comparative Formulation 3.

These Examples demonstrate that the compositions according to the invention makes it possible to achieve an acceptable compromise between viscosity of the composition, foaming properties and conditioning.

The invention claimed is:

1. A sulfate-free aqueous personal care composition comprising:
   i) from about 2 pbw to about 20 pbw of a surfactant system comprising at least:
      a) one methyl oleoyl taurate of formula $R^a CON(CH_3)CH_2CH_2SO_3X^a$, in which $R^a$ is the hydrocarbon radical of oleic acid and $X^a$ is a counterion,
      b) one isethionate of formula $R^b COOCH_2CH_2SO_3 X^b$, in which $R^b$ is a substituted or unsubstituted alkyl, alkenyl, aryl or alkylaryl group having 6 to 30 carbon atoms, and $X^b$ is a counterion, and
      c) one alkoxylated sulfosuccinate, and
   ii) from about 0.2 pbw to about 15 pbw of a conditioning agent.

2. The composition of claim 1, wherein the isethionate (b) is of formula $R^b COOCH_2CH_2SO_3\ X^b$, with $R^b$ being an unsubstituted alkyl group having 6 to 30 carbon atoms.

3. The composition of claim 2, wherein the isethionate (b) is of formula $R^b COOCH_2CH_2SO_3\ X^b$, with $R^b$ being an unsubstituted alkyl group having 7 to 24 carbon atoms.

4. The composition of claim 3, wherein the isethionate (b) is of formula $R^b COOCH_2CH_2SO_3\ X^b$, with $R^b$ being an unsubstituted alkyl group having 7 to 21 carbon atoms.

5. The composition of claim 1, wherein the alkoxylated sulfosuccinate (c) is an alkoxylated sulfosuccinate of formula $R^c—O—(CH_2CH_2O)_n C(O)CH_2CH(SO_3X^c)CO_2X^c$, wherein n ranges from 1 to 20, $R^c$ is a substituted or unsubstituted alkyl, alkenyl, aryl or alkylaryl group having 6 to 30 carbon atoms, and $X^c$ is a counterion.

6. The composition of claim 1, wherein the alkoxylated sulfosuccinate (c) is an alkoxylated sulfosuccinate of formula $R^c—O—(CH_2CH_2O)_n C(O)CH_2CH(SO_3X^c)CO_2X^c$, wherein n ranges from 2 to 20, $R^c$ is an unsubstituted alkyl group having 6 to 30 carbon atoms, for instance 7 to 24 carbon atoms, for instance 7 to 21 carbon atoms, and $X^c$ is a counterion.

7. The composition of claim 1, wherein the composition further comprises one amphoteric or zwitterionic surfactant selected from the group consisting of (1) amphoacetates and diamphoacetates, (2) sultaines and (3) alkylbetaines.

8. The composition of claim 1, wherein the weight ratio of alkoxylated sulfosuccinate (c) to methyl oleoyl taurate (a) is greater than or equal to 1, based on the weight percent of each surfactant in the final composition.

9. The composition of claim 8, wherein the weight ratio of alkoxylated sulfosuccinate (c) to methyl oleoyl taurate (a) is greater than 1, based on the weight percent of each surfactant in the final composition.

10. The composition of claim 1, wherein the weight ratio of alkoxylated sulfosuccinate (c) to isethionate (b) is greater than or equal to 1, based on the weight percent of each surfactant in the final composition.

11. The composition of claim 10, wherein the weight ratio of alkoxylated sulfosuccinate (c) to isethionate (b) is greater than 1, based on the weight percent of each surfactant in the final composition.

12. The composition of claim 1, wherein the total amount of surfactants ranges from 5 to 15 pbw, relative to the total weight of the composition.

13. The composition of claim 1, wherein the conditioning agent is a cationic or ampholytic conditioning agent.

14. The composition of claim 1, characterized in that it is a personal care cleansing composition.

15. A method comprising washing keratin substrates using the composition according to claim 1.

16. The method of claim 15, wherein the keratin substrates are the hair or the scalp.

* * * * *